(12) United States Patent
Berge et al.

(10) Patent No.: US 7,902,399 B2
(45) Date of Patent: Mar. 8, 2011

(54) FATTY ACIDS ANALOGOUS

(75) Inventors: Rolf Berge, Bønes (NO); Leiv K. Sydnes, Rådal (NO); Jon Songstad, Bergen (NO)

(73) Assignee: Thia Medica AS, Bergen (NO)

( * ) Notice: Subject to any disclaimer, the term of this patent is extended or adjusted under 35 U.S.C. 154(b) by 335 days.

(21) Appl. No.: 10/220,502

(22) PCT Filed: Mar. 2, 2001

(86) PCT No.: PCT/NO01/00082
§ 371 (c)(1),
(2), (4) Date: Nov. 12, 2002

(87) PCT Pub. No.: WO01/68582
PCT Pub. Date: Sep. 20, 2001

(65) Prior Publication Data
US 2004/0213442 A1    Oct. 28, 2004

(30) Foreign Application Priority Data
Mar. 3, 2000    (NO) .................................... 20001123

(51) Int. Cl.
*A01N 37/00*    (2006.01)
*C07C 57/02*    (2006.01)
(52) U.S. Cl. ........................................ 562/598; 514/558
(58) Field of Classification Search .................. 562/512, 562/598, 602, 556, 557, 606
See application file for complete search history.

(56) References Cited

U.S. PATENT DOCUMENTS 3,910,790 A    10/1975    Lohmer et al.

(Continued)

FOREIGN PATENT DOCUMENTS
DE    2210230    * 9/1973

(Continued)

OTHER PUBLICATIONS

Organometallics (2000), 19(1), 105-107.*

(Continued)

*Primary Examiner* — Karl J Puttlitz
(74) *Attorney, Agent, or Firm* — Finnegan, Henderson, Farabow, Garrett & Dunner, LLP

(57) ABSTRACT

The present invention relates to novel fatty acid analogous of the general formula (I): $R_1-[x_i-CH_2]_n-COOR_2$ wherein $R_1$ is: a $C_6-C_{24}$ alkene with one or more double bonds and/or with one or more triple bonds, and/or a $C_6-C_{24}$ alkyne, and/or a $C_6-C_{24}$ alkyl substituted in one or several positions with one or more compounds selected from the group comprising fluoride, chloride, hydroxy, $C_1-C_4$ alkoxy, $C_1-C_4$ alkylthio, $C_2-C_5$ acyloxy or $C_1-C_4$ alkyl, and wherein R2 represents hydrogen or $C_1-C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, and with the proviso that if R1 is an alkye, then the carbon-carbon triple bond is positioned between the (ω-1) carbon and the (ω-2) carbon, or between the (ω-2) carbon and the (ω-3) carbon, or between the (ω-3) carbon and the (ω-4) carbon, a salt, prodrug or complex thereof, which can be used for the treatment and/or prevention of syndrome X, obesity, hypertension, fatty liver, diabetes, hyperglycaemia, hyperinsulinemia and stenosis. Further, the invention relates to a nutritional composition comprising said fatty acid analogues, and a method for reducing the total weight, or the amount of adipose tissue in an animal.

14 Claims, 2 Drawing Sheets

U.S. PATENT DOCUMENTS

| | | | |
|---|---|---|---|
| 5,093,365 A * | 3/1992 | Berge et al. | 514/550 |
| 5,151,534 A | 9/1992 | Shroot et al. | |
| 5,268,494 A * | 12/1993 | Shroot et al. | 554/42 |
| 5,290,960 A | 3/1994 | Singh | |
| 6,365,628 B1 * | 4/2002 | Berge | 514/546 |
| 6,511,670 B1 * | 1/2003 | Maignan et al. | 424/401 |
| 7,375,135 B2 | 5/2008 | Najib-Fruchart et al. | |
| 2002/0188023 A1 | 12/2002 | Jorgensen et al. | |
| 2004/0219202 A1 | 11/2004 | Fletcher et al. | |
| 2007/0009608 A1 | 1/2007 | Berge | |
| 2007/0015795 A1 | 1/2007 | Berge | |

FOREIGN PATENT DOCUMENTS

| | | |
|---|---|---|
| EP | 0 250 994 | 1/1988 |
| EP | 0622 370 A2 | 7/1988 |
| EP | 0345 038 A2 | 5/1989 |
| EP | 0 342 115 B1 | 11/1989 |
| EP | 0 447 553 | 9/1991 |
| EP | 1 044 966 B1 | 9/2004 |
| JP | 49102616 * | 9/1974 |
| JP | 3-079659 | 4/1991 |
| NO | 20001905 | 10/2000 |
| WO | WO 93/21191 A1 | 10/1993 |
| WO | WO 96/11908 | 4/1996 |
| WO | WO 97/03663 | 2/1997 |
| WO | WO 99/58120 | 11/1999 |
| WO | WO 99/58121 | 11/1999 |
| WO | WO 99/58122 | 11/1999 |
| WO | WO 99/58123 | 11/1999 |
| WO | WO 00/30444 | 6/2000 |
| WO | WO 02/03983 A1 | 1/2002 |
| WO | WO 02/26218 | 4/2002 |
| WO | WO 02/43728 | 6/2002 |
| WO | WO 03/014073 A1 | 2/2003 |
| WO | WO 2004/000854 | 12/2003 |

OTHER PUBLICATIONS

Pearl et al., Lipids (1973), 8(11), 627-30.*
Abstract, Manabe et al., Chemical & Pharmaceutical Bulletin (1998), 46(2), 335-336, CAS online citation 128:217101 [retrieved Jan. 20, 2009] from STN; Columbus OH, USA.*
Marshall et al., Journal of Organic Chemistry (1992), 57(9), 2747-50.*
Abstract, Schwarz et al., Bioinorganic Chemistry (1973), 2(1), 47-68 (Schwarz), CAS online citation 80:10264 [retrieved Jan. 20, 2009] from STN; Columbus OH, USA.*
Guo et al., Journal of the Chemical Society, Chemical Communications (1991), (7), 479-81.*
Buist et al., Tetrahedron Letters (1988), 29(4), 435-8.*
Wu et al., Biochemical Pharmacology (1996), 51(6), 751-8.*
Yamamoto et al., "Cyclisation of Alkynecarboxylic Acids: Synthesis and Reactions of 6-Methylene-1,4-oxathian-2-ones and Their 4,4-Dioxides," *J. Chem. Research(M):* 0279-0296 12-13, compound 3a-3e (1990).
Koopmans et al., *Biochimica et. Biophysica. Acta* 1115: 230-238 (1992).
DeDuve et al.. *Biochem. J.* 60: 604-617 (1955).
Bremer J., *Biochimica et. Biophysics. Acta* 665: 628-631 (1981).
Chomczynski et al., *Anal. Biochem.* 162: 156-159 (1987).
Holm et al., *Biochimica et Biophysica. Acta*, 1006: 193-197 (1989).
Kikumasa et al., "A Synthesis of Dihydrothiopyran-3-ones. The Intramolecular Cyclization of Allylthioglycolic Acid Chlorides," *J. Org. Chem.* 36(15): 2077-2080 (1971).
Melo et al., "Intramolecular dipolar cyclo-additional reaction of 5H,7H-thiazolo(3,4-c)oxazol-4-1-olates: synthesis of chiral 1H-pyrrolo(1,2-c) thiazole derivatives," *J. Chem Soc. Perkin Trans.* 1: 1219-1223 (1999).
Wu et al., "Effects of Chain Length and Sulphur Position of Thia Fatty Acids on Their Incorporation into Phospholipids in 7800 C1 Hepatoma Cells and Isolated Rat Hepatocytes, and Their Effects on Fatty Acid Composition," *Biochemical Pharmacology* 51: 751-758 (1996).
Garras et al., *Biochimica et,. Biophysica. Acta* 1255: 154-160 (1995.

Willumsen et al., *J. Lipid Res.* 34: 13-22 (1993).
Clinkenbeard et al., *J. Biol. Chem.* 250: 3108-3116 (1975).
Vaagenes et al., *Biochem. Pharmacol.* 56: 1571-1582 (1998.
Woeltje et al., *J. Biol. Chem.*, 265: (18) 10720-10725 (1990).
Ayté et al., *Proc. Natl. Acad. Sci. USA*, 87: 3874-3878 (1990).
*J. Chem Research (M)*, 0273-0281, compound 3a-e (1990).
Esser et al., *J. Biol. Chem.* 268: 5817-5822 (1993).
Abdi-Dezfuli, F. et al. "Effects of Saturated and Polyunsaturated Fatty Acids and Their 3-Thia Fatty Acid Analogues on MCF-7 Breast Cancer Cell Growth" *Ann. of NY Acad. Sci.* (1994) 744:306-309.
Derwent English Abstract for EP 1044966, Derwent Week: 200101.
Derwent English Abstract for EP 342115, Derwent Week: 198946.
Derwent English Abstract for NO 200001905, Derwent Week: 200101.
English translation of JP S49-102616, published on Sep. 27, 1974.
Kundu A. et al. "Copper (II)/Tin (II) Reagent for Allylation, Propargylation, Alkynylation, and Benzylation of Diselenides: A Novel Bimetallic Reactivity" *Organometallics* (2000), 19:105-107.
Pearl, M. B. et al. "Acetylenic acids of *Alvaradoa amorphoides* seed oil" *Lipids* (1973) 8(11):627-30.
Office Action dated Nov. 18, 2008, from copending U.S. Appl. No. 10/518,427.
Lehninger, A. L., et al., *Principles of Biochemistry*, 2nd ed. (1993) Worth Publishers, Inc. pp. 246-251.
Runquist, E. A., et al., "Design, synthesis, and characterization of bis-phosphatidylcholine, a mechanistic probe of phosphatidylcholine transfer protein catalytic activity," *Biochimica et Biophysica Acta, Biomembranes* (1988) 940(1):10-12.
Bartnik, F. et al., "Film-forming, resorbable wound dressing containing oligomeric esters of lactic acid or glycolic acid," *Chemical Abstracts* (1989) 110(18):401-402.
Berge, R.K. et al., "Impact of cytochrome P450 system on lipoprotein metabolism. Effect of abnormal fatty acids (3-thia fatty acids)," *Pharmac. Ther.* (1994) 61:345-382.
Bestmann, H.J. et al., "Pheromones: 87. An Efficient Synthesis of (6E,11Z)-6,11-Hexadecadienyl Acetate and (6E,11Z)-6,11-Hexadecadienal: Female Sex Pheromone Components of *Antheraea pernyi* and *A. polyphemus* (Lepidoptera: Saturniidae)," *Synthesis* (1992) 1239-1241.
CAPLUS English Abstract of WO 03/014073 A1 Feb. 20, 2003.
Derwent English abstract for EP 0 250 994, WPI Acc No. 1988-000420.
Goodman & Gilman's *The Pharmacological Basis of Therapeutics* 10th Ed. (2001), McGraw Hill, NY, pp. 3-29.
Hasegawa, E. et al. "Polymerizable Glycerophosphocholines Containing Terminal 2,4-Hexadienyloxy Groups and Their Polymerized Vesicles," *Polymer Bulletin* (1986) 15(5): 397-403.
Hermetter, A. et al., "A Facile Procedure for the Synthesis of Saturated Phosphatidylcholines," *Chemistry and Physics of Lipids* (1981) 28:111-115.
Horiike, M. et al., "Synthesis of Insect Sex Pheromones and Their Homologues: (Z)-6-Alkenyl Acetates from the Wittig Reaction," *Agric. Biol. Chem.* (1978) 42(10):1963-1965.
Inami, K. et al. "Synthesis of Lysophosphatidylserine with 19:4 Acyl Group, as a Novel Sodium-Potassium ATPase Inhibitor, in Relation to DLIS-2, an Endogenous Digoxin-like Substance," *Tetrahedron Letters* (1990) 31(28):4033-4036.
Jayasuriaya, N. et al., "Design, Synthesis, and Activity of Membrane-Disrupting Bolaphiles," *JACS* (1990) 112:5844-5850.
Kurri, J. et al. "Bleaching composition," *Chemical Abstracts* (1991) 115:131.
Li, R. et al. "Sulfur-Substituted Phosphatidylethanolamines," *Journal of Organic Chemistry* (1993) 58(7): 1952-1954.
Markowitz, A.M. et al. "Microstructure formation properties of 1,2-bis(15-thia-pentacosa-10,12-diynoyl)-*sn*-3- phosphocholine: an acyl chain modified diacetylenic phospholipid," *Chemistry and Physics of Lipids* (1996) 84(1):65-74.
Molleyres, L.P. et al. "Structural Studies on the Diglyceride-mediated Activation of Protein Kinase C," *The Journal of Biological Chemistry* (1988) 263(29): 14832-14838.
Office Action from U.S. Appl. No. 10/518,427 dated Feb. 22, 2008.
Office Action from U.S. Appl. No. 10/518,427 dated Jul. 6, 2007.

Sharma, A. et al., "An Efficient Derivation of the Versatile Chiron Antipode 1-*tert*-Butyldimethylsilylpenta-1,4-diyn-3-ol: Application to the Synthesis of (15E,R,R,)-Duryne," *JOC* (1998) 63(18):6128-6131.

Skrede, S. et al. "Thia fatty acids, metabolism and metabolic effects," *Biochimica et Biophysica Acta* (1997) 1344:115-131.

Small, G. M. et al., "A sensitive spectrophotometric assay for peroxisomal acyl-CoA oxidase," *Biochem. J.* (1985) 227:205-210.

Tsujibo, H. et al. "Hypotensive Compounds Isolated from Alcohol Extract of the Unossified Horn of *Cervus elaphus* L. var. *xanthopygus* Milne-Edwarg (Rokujo). I. Isolation of Lysophosphatidyl Choline as a Hypotensive Principle and Structure-Activity Study of Related Compounds," *Chemical & Pharmaceutical Bulletin* (1987) 35(2): 365-359.

Wang, P. et al., "Synthesis of Phospholipid-Inhibitor Conjugates by Enzymatic Transphosphatidylation with Phospholipase D.," *JACS* (1993) 115:10487-10491.

Copending U.S. Appl. No. 10/518,427, filed Sep. 30, 2005.

Delfino, J. M., et al., "Synthesis of a Bipolar Phosphatidylethanolamine; A Model Compound for a Membrane-Spanning Probe," *Tetrahedron Lett.* (1987) 28(21):2323-26.

English language abstract of JP 3-079659, published on Apr. 4, 1991.

International Search Report for International Application No. PCT/GB2003/002582 dated Sep. 12, 2003.

Li, Ruoxin, et al., "Synthesis of Sulfur-Substituted Phosphatidylethanolamines and Inhibition of Protozoan Cyclopropane Fatty Acid Synthase," *Tetrahedron Lett.* (1993) 34(8):1279-82.

Markowitz, M. A and Singh, A, "Microstructure formation properties of 1,2-bis(15-thipentacosa-10,12-diynoyl)-sn-3-phosphocholine: an acyl chain modified diacetylenic phospholipid," *Chemistry and Physics of Liplds* (1996) 84:65-74.

Office Action in U.S. Appl. No. 10/518,427 dated Jul. 13, 2009.

Peterson. U. et al., "Origin of membrane dipole potential: Contribution of the phospholipid fatty acid chains," *Chemistry and Physics of Lipids* (2002) 117:19-27.

Abdi-Dezfuli, F. et al. "Effects of Saturated and Polyunsaturated Fatty Acids and Their 3-Thia Fatty Acid Analogues on MCF-7 Breast Cancer Cell Growth" *Ann. of NY Acad. Sci.* (1994) 744:306-309.

Derwent English Abstract for EP 1044966, Derwent Week: 200101, published Apr. 11, 2000.

Derwent English Abstract for EP 342115, Derwent Week: 198946, published May 9, 1989.

Derwent English Abstract for NO 200001905, Derwent Week: 200101, published Apr. 12, 2000.

Kundu A. et al. "Copper (II)/Tin (II) Reagent for Allylation, Propargylation, Alkynylation, and Benzylation of Diselenides: A Novel Bimetallic Reactivity" *Organometallics* (2000), 19:105-107.

Pearl, M. B. et al. "Acetylenic acids of *Alvaradoa amorphoides* seed oil" *Lipids* (1973) 8(11):627-30.

* cited by examiner

FATTY ACIDS ANALOGOUS

This application is a national stage application under §371 of international application no. PCT/NO01/00082, filed on Mar. 2, 2001, which claims the benefit of Norwegian Application No. 20001123, filed on Mar. 3, 2000.

FIELD OF THE INVENTION

The present invention relates to novel fatty acid analogous. Further, the invention relates to the use of the novel fatty acid analogous for the treatment and/or prevention of syndrome X, obesity, hypertension, fatty liver, diabetes, hyperglycaemia, hyperinsulinemia and stenosis. The invention also relates to processes for the preparation of the novel fatty acid analogues.

BACKGROUND OF THE INVENTION

EP 345.038 describes the use of non-β-oxidizable fatty acid analogues of the formula;

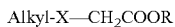

Alkyl-X—CH$_2$COOR wherein the alkyl is a saturated or unsaturated hydrocarbon chain of 8 to 22 carbon atoms, X represents a O, S, SO or SO2, and R is hydrogen or a C1-C4 alkyl group, for the treatment of hyperlipaemic conditions and for the reducing the concentration of cholesterol and triglycerides in the blood of mammals.

PCT/NO95/00195 describes alkyl-S—CH$_2$COOR and alkyl-Se—CH$_2$COOR for the inhibition of the oxidative modification of LDL. Further, this application describes the use of the selenium-compound for the treatment of hyperlipaemic condition and for reducing the concentration of cholesterol and trigylcerides.

The PCT applications PCT/NO99/00135, PCT/NO99/00136 and PCT/NO99/00149 describes fatty acid analogous of the formula (I)

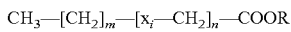

CH$_3$—[CH$_2$]$_m$—[x$_i$—CH$_2$]$_n$—COOR wherein n is an integer from 1 to 12, and
wherein m is an integer from 0 to 23, and
wherein i is an odd number which indicates the position relative to COOR, and
wherein X$_i$ independent of each other are selected from the group comprising O, S, SO, SO$_2$, Se and CH$_2$, and
wherein R represents hydrogen or C$_1$-C$_4$ alkyl,
with the proviso that at least one of the X$_i$ is not CH$_2$,
or a salt, prodrug or complex thereof.

This formula comprises one or several X groups (preferably selenium and sulphur) in positions 3, 5, 7, 9, etc.

Further, these PCT applications describe several medicinal and nutritional applications.

PCT/NO99/00135 describes the use of the fatty acid analogues the treatment and/or prevention of obesity, hypertension, fatty liver and the multi metabolic syndrome termed <<metabolic syndrome >> or Syndrome X. Further, this application describes a method for the treatment or prevention of an obese or overweight condition, and a method for producing weigh loss or a reduction of the fat mass in a human or non-human animal. The application also describes a nutritional composition effective to reduce, or to prevent an increase in, the total body weight or the total body fat mass in a human or non-human animal, and also a method for the modification of the fat distribution and content of animals in order to improve the quality of the meat, or product such as milk and eggs.

PCT/NO99/00136 describes use of fatty acid analogues for the treatment and/or prevention of diabetes (both type I and II), and a method for the treatment or prevention of hyperglycaemia, hyperinsulinemia and reduced sensitivity to insulin. A nutritional composition effective to reduce, or to prevent an increase in the concentration of glucose in the blood of a human or non-human animal is also disclosed, as is a method for reducing the concentration of glucose in the blood of a human or non-human animal.

PCT/NO99/00149 describes the use of the fatty acid analogues for the treatment and/or prevention of primary and/or secondary stenosis, and/or a disease caused by procedural vascular trauma and/or pathological proliferation of smooth muscle cells, and/or an increased level of plasma homocystein.

Due to the X-atom (most preferable sulphur or selenium) that is substituted in the carbon chain of the above given fatty acid analogues, these compounds will not be β-oxidized in the mitochondria beyond this position. Thus, the degradation of these molecules must start from the methyl end of the fatty acid, and this is a rather slow metabolic process. The catabolism of these fatty acid analogues includes ω-oxidation and chain shortening of the dicarboxylic acid by peroxisomes. Enzymes in the endoplasmic reticulum will ω-hydroxylate and further oxidise the hydroxylated fatty acid to a dicarboxylic acid. This acid may then be chain shortened by β-oxidation in the peroxisomes. Studies in rats have shown that 50% of the analogue TTA was excreted in the urine as short sulfoxy dicarboxylic acids within 24 hours of administration. In similar experiments it has been found that a desaturated product of TTA is formed in vivo. This is due to the microsomal enzyme Δ$^9$-desaturase which inserts a double bond in the 9-position of saturated fatty acids.

It is anticipated that this desaturated product has similar effects, and/or mediates the biological effects of the saturated fatty acid analogues. It is also likely that the biological effects of fatty acid analogues may be potentiated by slowing down their catabolism. This can be done by inserting double and/or triple bonds near the methyl end of the fatty acids, and/or by incorporating alkyl groups or halogens in this part of the molecule. Such molecules, i.e. the compounds in accordance with the present invention, will not be substrates for the relevant microsomal enzymes.

Obesity, and Related Diseases

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

It is therefore an object of the present invention to provide a treatment regimen that is useful in returning the body weight of obese subjects toward a normal, ideal body weight.

It is another object to provide a therapy for obesity that results in maintenance of the lowered body weight for an extended period of time. Further, it is an object to reduce or inhibit the weight gain normally induced by fat rich diets.

It is yet another object to prevent obesity and, once treatment has begun, to arrest progression or prevent the onset of diseases that are the consequence of, or secondary to, the obesity, such as hypertension and fatty liver. These and other objects will be apparent to those of ordinary skill in the art.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity.

It is also an object of the present invention to provide a treatment regimen that is useful in lowering the blood pressure.

Further, it is an object of the present invention to provide a treatment regimen that is useful in lowering the concentration of triacylglycerols in the liver. It is anticipated that such a regimen will provide an inhibiting effect on the development of a fatty liver condition, and also be suited as a method for the treatment of the manifested disease.

The compounds of the present invention activate the β-oxidation, and also reduce the concentration of triglycerieds in the liver.

The term "metabolic syndrome" is used to describe a multi-metabolic syndrome which is inter alia characterized by hyperinsulinemia, insulin resistance, obesity, glucose intolerance, Type 2 diabetes mellitus, dyslipidemia or hypertension.

As indicated above it is anticipated that the compounds of the present invention will provide a positive effect on all the conditions mentioned above, i.e. by regulating both the glucose and lipid homeostasis, and thus it is anticipated that the compounds of the present invention will be suitable agents for the regulation of the above defined metabolic disease (sometimes called syndrome X).

Diabetes

There are two major forms of diabetes mellitus. One is type I diabetes, which is also known as insulin-dependent diabetes mellitus (IDDM), and the other is type II diabetes, which is also known as noninsulin-dependent diabetes mellitus (NIDDM). Most patients with IDDM have a common pathological picture; the nearly total disappearance of insulin-producing pancreatic beta cells which results in hyperglycemia.

Considerable evidence has been accumulated showing that most IDDM is the consequence of progressive beta-cell destruction during an asymptomatic period often extending over many years. The prediabetic period can be recognized by the detection of circulating islet-cell autoantibodies and insulin autoantibodies.

There is a need for a compound which would be nontoxic and have no side effects but which would prevent clinical IDDM and NIDDM.

Type I diabetes: severe diabetes mellitus, usually of abrupt onset prior to maturity, characterized by low plasma insulin levels, polydipsia, polyuria, increased appetite, weight loss and episodic ketoacidosis; also referred to as IDDM.

Type II diabetes: an often mild form of diabetes mellitus, often of gradual onset, usually in adults, characterized by normal to high absolute plasma insulin levels which are relatively low in relation to plasma glucose levels; also referred to as NIDDM.

Type I and II diabetes are in accordance with an etiologic classification considered as <<primary>> diabetes respectively.

Secondary diabetes comprises pancreatic, extrapancreatic/ endocrine or drug-induced diabetes. Further, some types of diabetes are classified as exceptional forms. These include lipoatrophic, myatonic diabetes, and a type of diabetes caused by disturbance of insulin receptors.

Considering the high prevalence of diabetes in our society and the serious consequences associated therewith as discussed above, any therapeutic drug potentially useful for the treatment and prevention of this disease could have a profound beneficial effect on their health. There is a need in the art for a drug that will reduce the concentration of glucose in the blood of diabetic subjects without significant adverse side effects.

It is therefore an object of the present invention to provide a treatment regimen that is useful in lowering the blood glucose and to treat a diabetic condition.

It is yet another object of the invention to provide a treatment regimen that is useful in lowering the concentration of insulin in the blood, and to increase the effect of the remaining insulin.

Stenosis

Many pathological conditions have been found to be associated with smooth muscle cell proliferation. Such conditions include restenosis, arteriosclerosis, coronary heart disease, thrombosis, myocardial infarction, stroke, smooth muscle neoplasms such as leiomyoma and leiomyosarcoma of the bowel and uterus and uterine fibroid or fibroma.

Over half a million interventional intravascular procedures are performed each year. While such invasive procedures continue to improve over time, as many as 30-50% of the procedures performed each year fail as a result of restenosis, i.e. the formation of secondary stenosis. The reduction of restenosis is, therefore, often cited as the most critical factor in increasing the success realised in the treatment of cardiovascular disease through the use of interventional intravascular procedures, such as angioplasty, atherectomy, and procedures utilising stents and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using x-ray visualization. The deflated balloon is advanced until it reaches the site of the luminal narrowing, at which point the physician inflates the balloon one or more times to a pressure of about 4-6 atm for about 60 sec. When inflated, the balloon cracks and fractures the plaque and stretches the muscle fibre in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterised by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2-3 days of these procedures and to proliferate for several days thereafter (intimal hyperplasia).

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilisation and proliferation. It would be highly advantageous to develop new compositions or methods for inhibiting stenosis, restenosis or related disorders due to proliferation and mobilisation of vascular smooth muscle cells following, for example, traumatic injury to vessels rendered during vascular surgery.

It is anticipated that the compounds in accordance with the present invention will be effectively it the treatment of these diseases.

DETAILED DESCRIPTION OF THE INVENTION

The present invention relates to novel fatty acid analogues of the general formula (I):

$R_1$—[$x_i$—$CH_2$]$_n$—$COOR_2$     (I)

wherein $R_1$ is;
- a $C_6$-$C_{24}$ alkene with one or more double bonds and/or with one or more triple bonds, and/or
- a $C_6$-$C_{24}$ alkyne, and/or
- a $C_6$-$C_{24}$ alkyl substituted in one or several positions with one or more compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl, and wherein R2 represents hydrogen or $C_1$-$C_4$ alkyl, and
wherein n is an integer from 1 to 12, and
wherein i is an odd number and indicates the position relative to $COOR_2$, and
wherein $X_i$ independent of each other are selected from the group comprising O, S, SO, $SO_2$, Se and $CH_2$, and
with the proviso that at least one of the $X_i$ is not $CH_2$, and
with the proviso that if R1 is an alkyne, then the carbon-carbon triple bond is positioned between the (ω-1) carbon and the (ω-2) carbon, or between the (ω-2) carbon and the (ω-3) carbon, or between the (ω-3) carbon and the (ω-4) carbon, or a salt, prodrug or complex thereof.

Another aspect of the present invention relates to novel fatty acid analogues wherein the R moiety comprises one carbon-carbon double bond. A preferred embodiment relates to a fatty acid analogue wherein the carbon-carbon double bond is in the 9-position and in a cis configuration.

Most preferred embodiments of the present invention relates to compounds of formula (I) wherein a sulphur or selenium is arranged in position 3.

Further, the invention also relates to processes for the preparation of a compound of the formula (I), wherein the compound is prepared as described in example 1.

The present invention also relates to the use of the compound of formula (I) as pharmaceutical and/or nutritional agents. It is anticipated that the present compounds will exhibit substantially the same biological activities as the prior art compounds described above, and the present invention thus relates to the use of the present compounds of formula (I) for the applications described in the indicated publications.

Thus, the present invention relates to the use of the compounds of the formula (I) for the preparation of a pharmaceutical composition for the treatment and/or prevention of a condition selected from the group comprising syndrome X, obesity, hypertension, fatty liver, diabetes, hyperglycaemia, hyperinsulinemia and stenosis.

Further, the invention relates to the use of a compound of the formula (I) for;
- lowering the concentration of cholesterol and triglycerides in the blood of mammals,
- inhibiting the oxidative modification of low density lipoprotein The present invention also relates to a nutritional composition of formula (I), effective to reduce, or to prevent an increase in the total body weight or the total body fat mass in a human or non-human animal, and a method for producing weigh loss or a reduction of the fat mass in a human or non-human animal in need thereof.

Figure Legends

Figure 1:
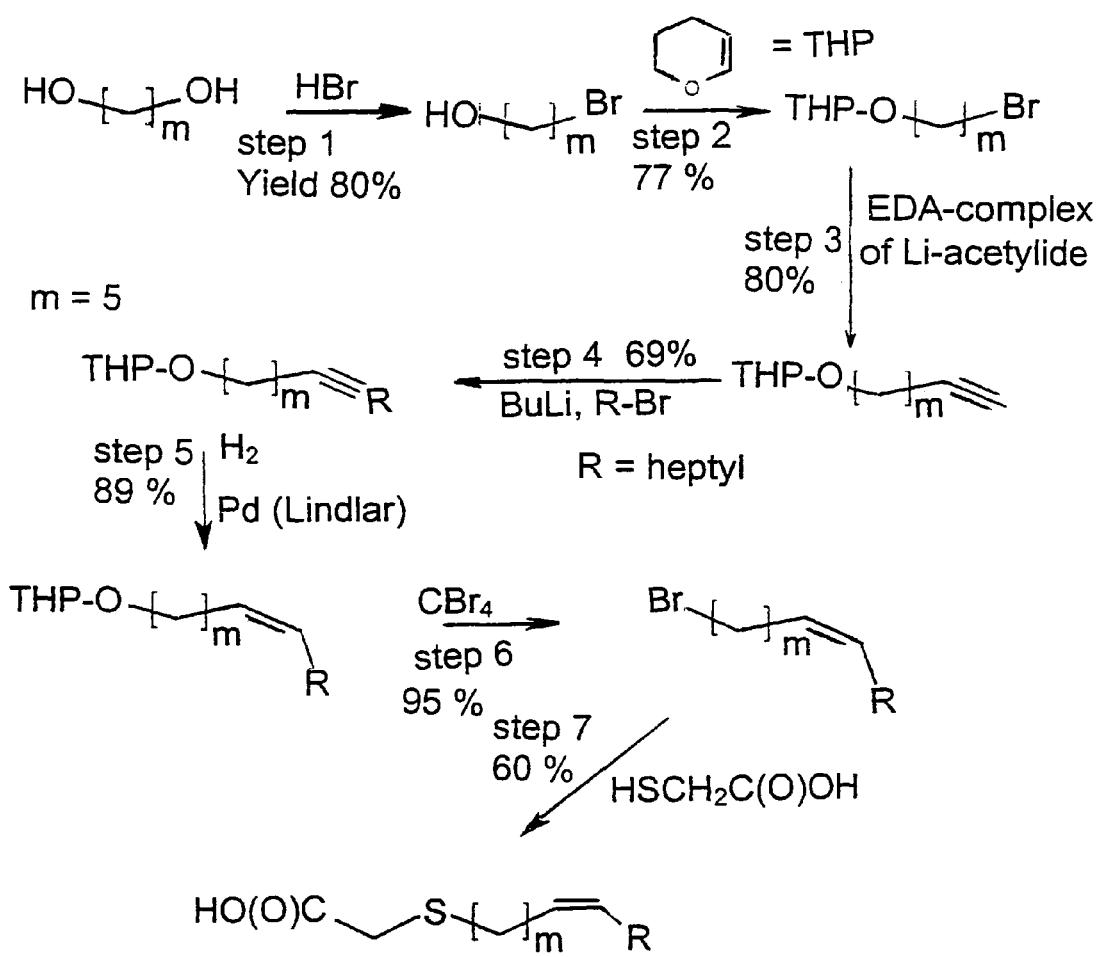
FIG. 1 shows a scheme for the synthesis of the compound (Z) 3-Thia-heptadec-9-enoic-acid.
Figure 2:
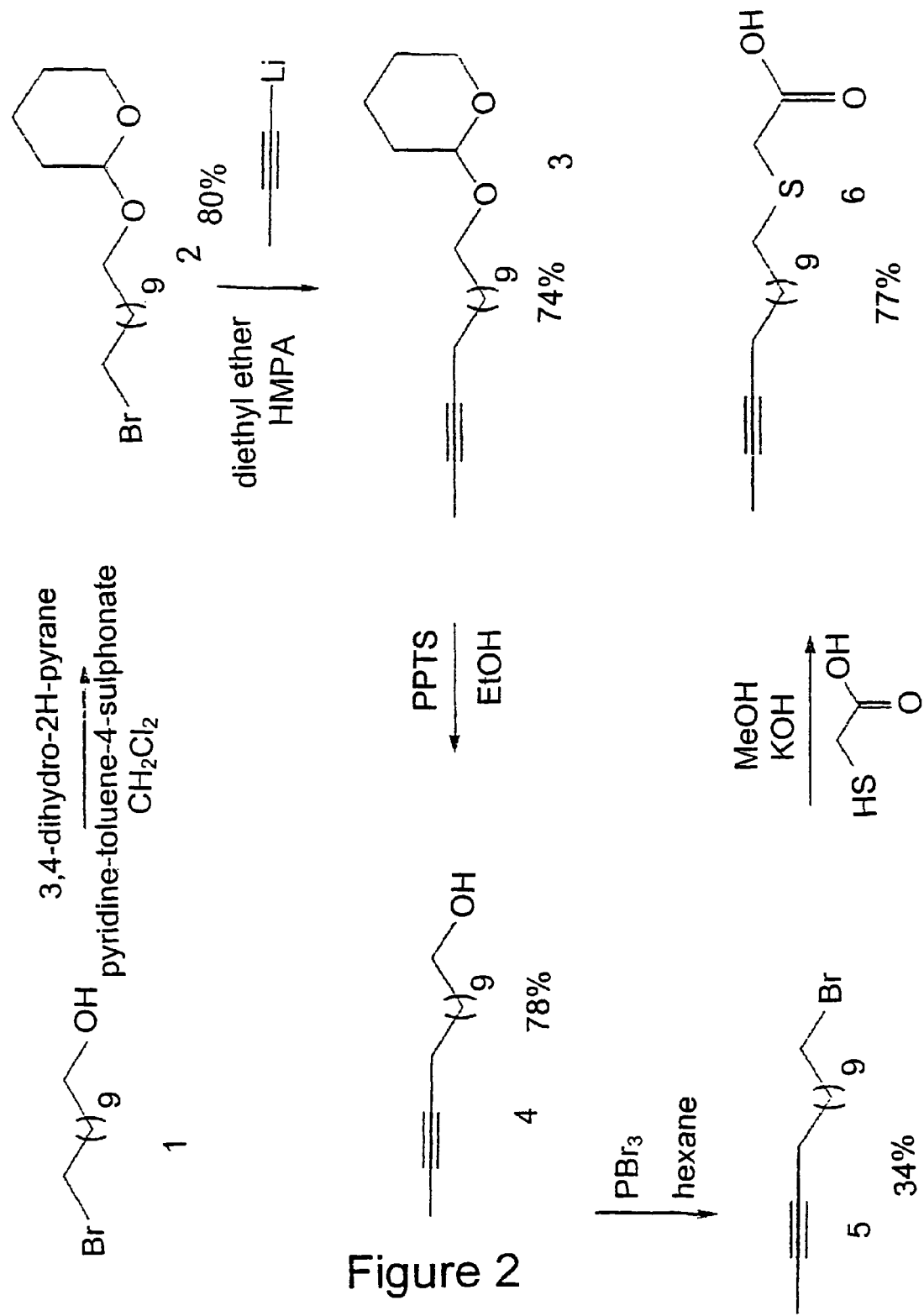
FIG. 2 shows a scheme for the synthesis of 3-thia-15-heptadecynoic acid.

Administration of the Compounds of the Present Invention

As a pharmaceutical medicament the compounds of the present invention may be administered directly to the animal by any suitable technique, including parenterally, intranasally, orally, or by absorption through the skin. They can be administered locally or systemically. The specific route of administration of each agent will depend, e.g., on the medical history of the animal.

The invention will be more fully understood by reference to the following examples. They should not, however, be construed as limiting the scope of the invention.

Experimental Section

Methods

The methods described below were used as test systems for the compounds described in the prior art, and are thus also be used to test the biological effects of the present compounds.
Obese Zucker (fa/fa) Rats.

The obese Zucker (fa/fa) rats used in this study were bred at the U 465 INSERM animal facility from pairs originally provided by the Harriet G. Bird Laboratory (Stow, Mass., USA). Unless otherwise stated, the animals were maintained under a constant light-dark cycle (light from 7:00 a.m. to 7:00 p.m.) at 21±1° C. and were given free access to food and water. Three rats were housed per cage. Weight gains were recorded daily.
Wistar Rats Male Wistar Charles River rats weighing 280-358 were purchased from AnLab Ltd. (Prague, Czech Repubic) and housed in wire-mesh cages in a temperature (22±1° C.) and light-controlled (light from 7.00 a.m. to 7.00 p.m.) room. They were given free access to chow and water. Three rats were housed per cage. Weight gain and food intake were recorded daily.
Intravenous Glucose Tolerance Tests Male Zucker (fa/fa) rats (5 weeks old) were anaesthetised after a 5-hours fast, by intraperitoneal injection of sodium pentobarbital (50 mg/kg). The rats were injected with glucose (0.55 g/kg) in the saphenous vein and blood samples were collected from the tail vein in heparinized tubes at time 0, 5, 10, 15, 20 and 30 minutes after the glucose load. Samples were kept on ice, centrifuged and plasma was stored at −20° C. until analysis.
Hyperinsulinemic Euglycemic Clamp.

After 21 days on their respective diets (see above), the rats were anaesthetised by injection of xylazine hydrochloride (Rometar SPOFA, Prague, Czech Republic; 10 mg/ml) and ketamine hydrochloride (Narkamon SPOFA, Prague, Czech Republic; 75 mg/ml), and fitted with chronic carotid artery and jugular vein cannulas as described by Koopmans et al. (Koopmans, S. J., et al., Biochim Biophys Acta, 1115, 2130-2138 1992.). The cannulated rats were allowed to recover for two days after surgery before the clamping studies which were carried out according to Kraegen et al. (Kraegen, E. W., et al., Am J Physiol, 248, E353-E362 1983.). Thus, on the third day after surgery, unrestrained conscious rats were given a continuous infusion of porcine insulin (Actrapid, Novo Nordisk, Denmark) at a dose of 6.4 mU per kg per min to achieve plasma insulin levels in the upper physiological range. The arterial blood glucose concentration was clamped at the basal fasting level, by variable infusion of a 30% w/v glucose solution (Leciva, Prague, Czech Republic). Blood samples for determination of plasma glucose and insulin concentrations were obtained every 15 minutes from the start of the glucose infusion. After 90 minutes, the rats were disconnected from the infusions and immediately decapitated, blood was collected for plasma separation, liver and epididymal adipose tissue pads were dissected out and weighed.

Measurement of Plasma Parameters

Glucose (GLU, Boehringer Mannheim, Germany), free fatty acids (NEFA, C ACS-ACOD kit; Wako Chemicals, Dalton, USA) and b-hydroxybutyrate (310-A kit; Sigma Diagnostics Inc., St. Louis, USA) concentrations were measured using enzymatic methods. Insulin concentrations were determined with radioimmunoassay by (CIS bio International, Gif sur Yvette, France) using rat insulin as standard in the Zucker rats. In the Wistar Charles River rats, plasma glucose concentrations were measured with the aid of Beckman Glucose Analyzer (Fullerton, Calif., USA). Plasma insulin levels were measured using a RIA kit from Linco Research Inc. (St. Charles, Mo., USA). Phospholipids were measured by the enzymatic method of bioMérieux, Marcy-l'Etoile, France, Triacylglycerol by the Technicon Method no. SA4-0324L90, USA and Cholesterol by the Technicon Method no. SA4-0305L90, USA.

Preparation of Post-nuclear and Mitochondrial Fractions and Measurement of Enzyme Activities Freshly isolated livers from individual old Zucker rats, were homogenised in ice-cold sucrose buffer (0.25 M sucrose, 10 mM HEPES (pH 7.4) and 2 mM EDTA). Post-nuclear and mitochondrial fractions were prepared using preparative differential centrifugation according to DeDuve et al. (De Duve, C., et al., Biochem. J., 60, 604-617 1955.) Modifications, purity and yield were as described earlier (Garras, A., et al., Biochim. Biophys. Acta, 1255, 154-160 1995.). Acid soluble products were measured in post-nuclear and mitochondrial enriched fractions, using [1-$^{14}$C]-palmitoyl-CoA and [1-$^{14}$C]-palmitoyl-L-carnitine (Radio-chemical Centre, Amersham, England) as substrates as described earlier (Willumsen, N., et al., J. Lipid Res., 34, 13-22 1993. Carnitine palmitoyltransferase-I and -II activities were measured in the post-nuclear and mitochondrial fractions essentially as described by Bremer (Bremer, J., Biochim. Biophys. Acta, 665, 628-631 1981.) and 3-hydroxy-3-methylglutharyl-CoA synthase was measured according to Clinkenbeard et al. (Clinkenbeard, K. D., et al., J. Biol. Chem, 250, 3108-3116 1975.) in the mitochondrial fractions.

RNA Analysis

RNA extraction (Chomczynski, P., et al., Anal. Biochem., 162, 156-159 1987.), Northern blot analysis and slot blotting of RNA onto nylon filters, and hybridisation to immobilised RNA were performed as earlier described (Vaagenes, H., et al., Biochem. Pharmacol., 56, 1571-1582 1998.). The following cDNA fragments were used as probes: CPT-I, (Esser, V. et al., J. Biol. Chem., 268, 5817-5822 1993), CPT-II (Woeltje, K. F., et al., J. Biol. Chem., 265, 10720-10725 1990.), 3-hydroxy-3-methylglutharyl-CoA synthase (Ayté, J., et al., Proc. Natl. Acad. Sci. USA., 87, 3874-3878 1990.), and hormone sensitive lipase (Holm, C., et al., Biochim. Biophys. Acta, 1006, 193-197 1989.). The relative levels of RNA expression were estimated as the amounts of radioactive probe hybridised to the respective levels of 28S rRNA.

Results

Example 1

Synthesis of Novel Fatty Acid Compounds

A) Non-β-oxidizable fatty acid analogous with a carbon-carbon double bond.

The synthesis of a compound in accordance with the present invention is representatively elaborated with reference to the synthesis of the thia-heptadec-9-enoic acid;

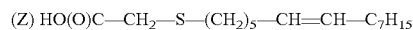

(Z) designates a cis configuration.

1. Preparation of 1-bromo-5-hydroxy-pentane

Pentane-1,5-diol, HO—(CH2)5-OH, was treated with HBr in benzene and refluxed for 24 h. The product mixture was chromatographed first with a 85:15 hexane-diethyl ether mixture to remove the dibromide and then with a 70:30 mixture. Yield of 1-bromo-5-hydroxy-pentane, 80%.

$^1$H-NMR: 1,81(—CH$_2$—CH$_2$OH), 1,44(—CH$_2$—), 3,35 (—CH$_2$—Br), 3,55(—CH$_2$—OH), 3,32(—OH), 1,51(—CH$_2$—CH$_2$Br).

$^{13}$C-NMR: 31,43-32,30(C$_2$,C$_4$), 24,24(C$_3$), 33,64(C$_5$), 62,11(C$_1$).

2. Preparation of 5-(tetrahydropyranyloxy)-1-bromopentane

This compound was allowed to react with 3,4-dihydro-2H-pyrane in CH$_2$Cl$_2$ at 0° C. 2 drops of conc. HCl was used as catalyst. After removal of the solvent the reaction product was chromatographed in 95:5 hexane-diethyl ether. The yield of 5-(tetrahydropyranyloxy)-1-bromopentane was 77%.

$^1$H-NMR: 1,45-1,63(—CH$_2$—), 1,83(—CH$_2$—CH$_2$O—), 3,38(—CH$_2$—Br), 3,27-3,79(—CH$_2$O—), 4,52(—O—CH—O).

$^{13}$C-NMR: 24,9-32,92(C$_2$-C$_4$), 33,61C$_5$), 62,26(C$_6$), 98,83 (C$_1$ in THP).

3. Preparation of 7-(tetrahydropyranyloxy)-1-heptyne

The product from step 2 was treated with the EDA complex of Li-acetylide in dry dimethyl sulfoxide at 0° C. under argon. After 4 h at room temperature the reaction mixture was hydrolysed with water and organic products extracted with diethyl ether. The residue after removing the ether was chromatographed in 97:3 hexane-diethyl ether, yielding 7-(tetrahydropyranyloxy)-1-heptyne in 62% yield.

$^1$H-NMR: 1,45-1,66(—CH$_2$—), 3,45-3,82(—CH$_2$—O), 2,16(—CH$_2$—C≡), 1,90(HC≡C—), 4,53(—O—CH—O—).

$^{13}$C-NMR: 18,27-30,66(C$_3$-C$_6$), 62,21(C$_7$), 68,14(C$_1$), 84,40(C$_2$).

4. Preparation of 1-(tetrahydropyranyloxy)-tetradec-6-yne

To a 1,6 M solution of BuLi in hexane dissolved in THF at 0° C. under argon and the product from 3 was added a mixture of 1-bromoheptane and N,N-dimethylpropyleneurea. After hydrolysis, extraction and chromatography 1-(tetrahydropyranyloxy)-tetradec-6-yne was isolated in 69% yield.

$^1$H-NMR: 0,85(CH$_3$—), 1,22-1,57(—CH$_2$—), 2,10(—CH$_2$—C≡), 3,30-3,84(—CH$_2$O—), 4,55(—O—CH—O—).

$^{13}$C-NMR: 14,02($C_{14}$), 22,60-31,73($C_2$-$C_{13}$), 18,69-18,71 ($C_5$ og $C_8$), 62,23($C_1$), 79,91-80,32($C_6$ og $C_7$).

5. Preparation of 1(Tetrahydropyranyloxy)-tetradec-6-ene

The substituted tetradec-6-yne from step 4 was reduced with hydrogen in the presence of the Lindlar catalyst in ethanol. The reduction lasted for 4 h. 1(Tetrahydro-pyranyloxy)-tetradec-6-ene appeared sufficiently pure for step 6 without further purification but could be isolated in 89% yield after chromatography.

$^1$H-NMR: 0,90($CH_3$—), 1,27-1,61(—$CH_2$—), 3,39-3,89 (—$CH_2$—O), 2,04(—$CH_2$—C=), 4,59(—O—CH—O—), 5,37 (—HC=CH—).

$^{13}$C-NMR: 14,07($C_{14}$), 22,65-31,85($C_2$-$C_{13}$), 62,27($C_1$), 27,13, 27,19($C_5$ and $C_8$), 129,60-130,04($C_6$ and $C_7$).

6. Preparation of 1-bromotetradec-6-ene

The product from 5 was brominated with $CBr_4$ at 0° C. in dichloromethane in the presence of $Ph_3P$. The reaction mixture was stirred overnight. The yield of 1-bromotetradec-6-ene was quantitative.

$^1$H-NMR: 0,87($CH_3$—), 1,27-1,52(—$CH_2$—), 2,01(—$CH_2$—C=), 3,39(—$CH_2$—Br), 1,45(—$CH_2$—$CH_2$—Br), 1,85(—$CH_2$—$CH_2$C=), 5,34(—HC=CH—).

$^{13}$C-NMR: 14,00($C_{14}$), 22,60-32,68($C_2$-$C_{13}$), 26,97, 27,24 ($C_5$ and $C_8$), 33,75($C_1$), 129,15-130,32($C_6$ and $C_7$).

7. Preparation of (Z)3-thia-heptadec-9-enoic acid

The bromodecene from step 6 in methanol was added to 3 equivalents of KOH and 1.5 equivalents of HS—$CH_2$—C(O)OH in methanol under argon during 30 min. After stirring at room temperature for 4 h, refluxing for another 12 h, followed by hydrolysis and extraction with diethyl ether, then acidifying to pH 1-2, the product, the title compound, was isolated as viscous oil in 60% yield.

The following analyses have been performed; IR, 600 MHz 1H and 13C NMR, MS, GC, GC-MS of the methyl ester. The NMR results are given below. All data are given in parts per million (ppm). No trace of the E-compound could be detected.

1H-NMR: 0.86 (CH3-), 1.16-1.60 (—CH2-), 1.99 (—CH2-C=), 2.64 (—CH2-S—), 3.22 (—S—CH2-C(O)OH), 5.33 (HC=CH).

13C-NMR: 176.63 (C1), 33.34 (C2), 32.69 (C4), 22.63-31.83 (C5-C7,C12-C16), 129.32 and 130.24 (C9, C10), 26.98 and 27.19 (C8, C11), 14.08(C17).

B) Non-β-oxidizable Fatty Acid Analogous Comprising a Carbon-carbon Triple Binding.

The synthesis of a compound in accordance with the present invention is representatively elaborated with reference to the synthesis of the 3-thia-15-heptadecynoic acid, as given in FIG. 1.

1. Preparation of 11-Bromo-1(tetrahydro-2-pyranyloxy) Undecane.

Pyridine toluene 4-sulphonate (1,0 g, 4,0 mmol) and 11-Bromo-1-undecanol (10,0 g, 400 mmol) were dissolved in dry CH2CH2 (200 ml) at ambient temperature, and 3,4-dihydro-2H-pyrane (5,0 g, 60 mmol) was added. The reaction mixture was stirred overnight. The crude product was purified by flash chromatography on silica gel eluted with $CH_2Cl_2$. The yield of 11-Bromo-1(tetrahydro-2-pyranyloxy)undecane was 10,7 g (80%).

2. Preparation of 14-(tetrahydro-2-pyranoyl)-2-tetradecyne.

Propyne gas was bubbled through a solution of MeLi in diethyl ether (0,8 M, 60 ml, 51,2 mmol) in a rate adapted to ensure reflux of the ether. When there were no longer any heat development, the reaction was considered finished (white slurry). 11-Bromo-1(tetrahydro-2-pyranyloxy) undecane (product 2) (13,0 g, 38,8 mmol) was added drop by drop to this solution over a period of 20 minutes. The reaction was stirred overnight, and water (50 ml) was carefully added drop by drop. The mixture was diluted with diethyl ether and washed with water (5×), dried (MgSO$_4$) and the solvent was evaporated off. The crude product was purified by flash chromatography with $CH_2Cl_2$ as eluent. The yield of 14-(tetrahydro-2-pyranoyl)-2-tetradecyne was 8,5 g (74%).

3. Preparation of 12-Tetradecyn-1-ol

Pyridine Toluene 4-Sulphonate (0,3 g, 1,2 mmol) and the alkyne (product 3) were dissolved in ethanol (25 ml) and heated to 50° C. overnight. The solvent was evaporated and distributed between water and $CH_2CL_2$. The water phase was washed with water, dried (MgSO$_4$) and the solvent was evaporated. The crude product was purified with flash chromatography with $CH_2Cl_2$ as eluent. The yield of 12-Tetradecyn-1-ol was 1,5 g (78%).

4. Preparation of 14-Bromo-2-tetradecyne 12-Tetradecyn-1-ol (5,0, 23,8 mmol) was dissolved in hexane (50 ml) and 10 drops of pyridine was added. $PBr_3$ was added to this mixture. The mixture was heated to 60° C. for three hours, cooled, and water was added drop by drop. The mixture was washed by water, dried (MgSO$_4$) and the solvent was evaporated. The crude product was purified with flash chromatography with hexane as eluent until 2,5% EtOAc in hexane. The yield of 14-Bromo-2-tetradecyne was 2,2 g (34%).

5. Preparation of 3-thia-15-heptadecynoic acid

KOH (2,76 g, 49,0 mmol) was dissolved in methanol (30 ml), and thioglycolic acid (2,04 g, 22,1 mmol) in methanol (25 ml) was added drop by drop. After 10 minutes the 14-Bromo-2-tetradecyne (5,5 g, 20,1 mmol) was carefully added drop by drop, and the mixture was heated to 50° C. overnight. The mixture was cooled to 0° C., and 30 ml HCl was added (pH=1). The precipitate was filtered and washed with water (2×). The solid material was dissolved in chloroform (100 ml) and washed with water (1×), dried (MgSO$_4$) and the solvent was evaporated off. The yield of the compound 3-thia-15-heptadecynoic acid was 4,4 g (77%).

$^1$H NMR (300 MHz, CDCl$_3$) δ: 1.26 (10 H, sharp m), 1.3-1.4(4 H, m), 1.46 (2 H, quint, J=7.0 Hz, =CCH$_2$CH$_2$—), 1.60 (2 H, quint, J=7.0 Hz, —CH$_2$CH$_3$S—), 1.77 (3 H, t, J=2.6 Hz, CH$_3$C=), 2.10(2 H, tq, J=2.6, 7.0 Hz. =CCH$_2$—), 2.65(2 H, t, J=7.3 Hz, —CH$_2$S—), 3.25 (2 H, s. —SCH$_2$COOH), 10.40 (1 H, broad s, —COOH).

$^{13}$C NMR (75 MHz, CDCl$_3$) δ: 3.35 (CH$_3$C=), 18.61 (=CCH$_2$—), 28.60, 28.78, 28.78, 28.97, 29.04, 29.04, 29.34, 29.38, 29.40, 32.70 (—CH$_2$CH$_2$S—), 33.34 (—SCH$_2$CO), 75.20 (MeC≡C—), 79.31 (MeC≡C—), 176.42 (CO).

C) Non-β-oxidizable Fatty Acid Analogous Substituted in One or Several Positions.

One or several of the hydrogen groups of the fatty acid chain can be substituted with one or more of the compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl. The substituents can for instance be incorporated in the formula (I) compound by selecting other substrates in the steps 1-4 above.

Finally, the compounds prepared in step (C) above can be converted to saturated compounds with a traditionally hydrogenation reaction, thus giving an R1 group which is fully saturated (i.e. an alkyl), but substituted at one or more positions.

EXAMPLE 2

Toxicity Study of TTA

Toxicity studies, and test for mutagenic activity will be performed as described in PCT/NO99/00135.

EXAMPLE 3.

The biological activity of the novel compounds in accordance with the present invention will be determined as described in the experimental section above, or as disclosed in the publications cited above.

The invention claimed is:

1. A method for producing weight loss or a reduction of the fat mass in a human or non-human animal in need thereof, comprising administering thereto, an effective amount of a composition comprising a compound according to the general formula (I):

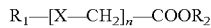

wherein $R_1$ is;
a $CH_3$—$R_3$, wherein $R_3$ is a $C_5$-$C_{24}$ alkene with one or more double bonds,
a $CH_6$-$C_{24}$ alkyne, with one or more triple bonds, or
a $C_6$-$C_{24}$ alkyl substituted in one or more positions with one or more substituents chosen from fluoride, chloride, hydroxy, $C_1$-$C_4$ alkoxy, $C_1$-$C_4$ alkylthio, and $C_2$-$C_5$ acyloxy, and
wherein $R_2$ represents hydrogen or $C_1$-$C_4$ alkyl,
wherein n is an integer from 1 to 12, and
wherein X are independently chosen from S, SO, $SO_2$, Se and $CH_2$, with the proviso that at least one of the X is not $CH_2$, and
with the proviso that if $R_1$ is an alkyne, then at least one carbon-carbon triple bond is positioned between the ($\omega$-1) carbon and the ($\omega$-2) carbon, or between the ($\omega$-2) carbon and the ($\omega$-3) carbon, or between the ($\omega$-3) carbon and the ($\omega$-4) carbon,
or a pharmaceutically acceptable salt thereof.

2. A fatty acid analogue, wherein the fatty acid analogue is 3-thia-15-heptadecynoic acid or a pharmaceutically acceptable salt, or prodrug thereof.

3. A process for the preparation of a non-β-oxidizable fatty acid analogue according to claim 2, comprising:
preparation of 11-bromo-1 (tetrahydro-2-pyranyloxy)undecane by reacting pyridine toluene 4-sulphonate and 11-bromo-1-undecanol with 3,4-dihydro-2H-pyran;
adding the 11-bromo-1-undecanol with 3,4-dihydro-2H-pyran to a solution comprising propyne gas, MeLi and diethyl ether to yield 14-(tetrahydro-2H-pyranoyl)-2-tetradecyne;
hydroxylation of the 14-(tetrahydro-2H-pyranoyl)-2-tetradecyne using ethanol in a suitable organic solvent to yield 12 tetradecyn-1-ol;
preparation of 14-bromo-2-tetradecyne by reacting the 12-tetradecyn-1-ol dissolved in hexane with pyridine and $PBr_3$;
preparation of 3-thia-15-heptadecynoic acid by reacting the 14-bromo-2-tetradecyne with KOH and thioglycolic acid in methanol.

4. A method for the treatment of a condition chosen syndrome X, obesity, hypertension, fatty liver, diabetes, hyperglycaemia, hyperinsulinemia and stenosis comprising administering to a patient in need thereof, an effective amount of a composition comprising a compound according the general formula (I):

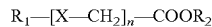

wherein $R_1$ is;
a $CH_3$—$R_3$, wherein $R_3$ is a $C_5$-$C_{24}$ alkene with one or more double bonds,
a $C_6$-$C_{24}$ alkyne, with one or more triple bonds, or
a $C_6$-$C_{24}$ alkyl substituted in one or more positions with one or more substituents chosen from fluoride, chloride, hydroxy, $C_1$-$C_4$ alkoxy, $C_1$-$C_4$ alkylthio, and $C_2$-$C_5$ acyloxy, and
wherein $R_2$ represents hydrogen or $C_1$-$C_4$ alkyl, wherein n is an integer from 1 to 12, and
wherein X are independently chosen from S, SO, $SO_2$, Se and $CH_2$, with the proviso that at least one of the X is not $CH_2$, and
with the proviso that if $R_1$ is an alkyne, then at least one carbon-carbon triple bond is positioned between the ($\omega$-1) carbon and the ($\omega$-2) carbon, or between the ($\omega$-2) carbon and the ($\omega$-3) carbon, or between the ($\omega$-3) carbon and the ($\omega$-4) carbon,
or a pharmaceutically acceptable salt thereof.

5. A pharmaceutical composition comprising the compound according to claim 2, and a pharmaceutically acceptable carrier.

6. A nutritional composition comprising the compound according to claim 2, and a nutritionally acceptable carrier.

7. A method for producing weight loss or a reduction of the fat mass in a human or non-human animal in need thereof, comprising administering thereto, and effective amount of a composition comprising the compound according to claim 2.

8. A method for the treatment of a condition chosen syndrome X, obesity, hypertension, fatty liver, diabetes, hyperglycaemia, hyperinsulinemia and stenosis comprising administering to a patient in need thereof, an effective amount of a composition comprising the compound according to claim 2.

9. The method according to claim 1, wherein the $R_1$ moiety comprises one carbon-carbon triple bond.

10. The method according to claim 1, wherein the $R_1$ moiety comprises one carbon-carbon double bond.

11. The method according to claim 1, wherein the X is sulfur.

12. A The method according to claim 1, wherein the X is selenium.

13. A The method according to claim 1, wherein the carbon-carbon double bond is in a cis configuration.

14. A The method according to claim 13, wherein said carbon-carbon double bond is in the 9-position.

* * * * *